United States Patent [19]

Tobin

[11] 4,107,377

[45] Aug. 15, 1978

[54] PROCESS FOR PRODUCING 3-TRICHLOROMETHYL-5-LOWERALK-YLAMINO-1,2,4-THIADIAZOLE

[75] Inventor: John H. Tobin, Winsted, Conn.

[73] Assignee: Olin Corporation, New Haven, Conn.

[21] Appl. No.: 821,024

[22] Filed: Aug. 1, 1977

[51] Int. Cl.$^2$ .......................................... C07D 285/08
[52] U.S. Cl. ............................................. 260/306.8 D
[58] Field of Search ................................ 260/306.8 D

[56] References Cited

PUBLICATIONS

Goerdeler, *Chemische Berichte*, 1954, pp. 57–67.

*Primary Examiner*—Alton D. Rollins
*Attorney, Agent, or Firm*—William A. Simons; Thomas P. O'Day

[57] ABSTRACT

A process for producing 3-trichloromethyl-5-loweralkylamino-1,2,4-thiadiazole compounds by the reaction of a N-loweralkylisothiocyanate with a N-halotrichloroacetamidine in the presence of a base. The N-halotrichloroacetamidine compound may be added to the reaction mixture or, instead, generated in situ.

22 Claims, No Drawings

PROCESS FOR PRODUCING 3-TRICHLOROMETHYL-5-LOWERALKYLAMINO-1,2,4-THIADIAZOLE

BACKGROUND OF THE INVENTION

1. Field of the Invention

This invention relates to a process for making 3-trichloromethyl-5-loweralkylamino-1,2,4-thiadiazole compounds.

2. Description of the Prior Art

3-Trichloromethyl-5-loweralkylamino-1,2,4-thiadiazole compounds are known as effective soil fungicides. See U.S. Pat. Nos. 3,260,588 and 3,260,725, both of which were issued to H. A. Schroeder on July 12, 1966. These compounds are also known as chemical intermediates in making N-3-trichloromethyl-1,2,4-thiadiazolyl (5)]-N,N'-di-loweralkylureas, which may be utilized as herbicides and nitrification inhibitors. See U.S. Pat. No. 3,822,280, issued to Hans Moser et al on July 2, 1974. Also see *Chemical Abstracts*, Vol. 76: 31239h and vol. 78: 70742c.

As noted in the above-cited Schroeder patents, these 3-trichloromethyl-5-loweralkylamino-1,2,4-thiadiazole compounds have been prepared by reacting trichloromethylacetamidine or its hydrochloride with trichloromethanesulfenyl chloride in the presence of alkali and an inert immiscible organic solvent to form 3-trichloromethyl-5-chloro-1,2,4-thiadiazole. This 5-chloro compound is then reacted with the appropriate loweralkylamine in benzene solvent in order to substitute a loweralkylamino group for the chloro group in the 5-position.

This prior art process for making these compounds, however, has certain commercially disadvantageous features. Particularly, this process requires more than one solvent. Thus, a solvent exchange step and an intermediate product isolation step are necessary. More importantly, the overall yields of the product are relatively low. Therefore, it would be advantageous if a new process for making these compounds was developed whereby only one solvent would be necessary and a higher overall yield of product was obtained.

BRIEF SUMMARY OF THE INVENTION

The present invention is directed to a process for making 3-trichloromethyl-5-loweralkylamino-1,2,4-thiadiazole compounds by the reaction of a N-loweralkylisothiocyanate with a N-halotrichloroacetamidine in the presence of a base. The N-halotrichloroacetamidine compound may be simply added to the reaction mixture or, instead, generated in situ.

The 3-trichloromethyl-5-loweralkylamino-1,2,4-thiadiazole compounds so produced may be employed as effective fungicides and the like or may be reacted with a loweralkylisocyanate to form N-[3-trichloromethyl-1,2,4-thiadiazolyl (5)]-N-N'-di-loweralkylureas.

DETAILED DESCRIPTION

The process of the present invention encompasses the reaction of an N-loweralkylisothiocyanate compound with an N-halotrichloroacetamidine compound in the presence of base to form a 3-trichloromethyl-5-loweralkylamino-1,2,4-thiadiazole. This reaction is illustrated by equation (3) shown below and is believed to form a short-lived N-(trichloromethyl-N'-haloimido)-N"-)loweralkyl)thiourea intermediate that is shown in brackets. The lower alkyl group in the N-loweralkylisothiocyanante compound may be any alkyl group containing 1-4 carbon atoms. The halo group in the N-halotrichloroacetamidine compound may be either a chloro-, bromo-, or iodo-group. It is preferred to use N-methylisothiocyanate because the known effective pesticide N-[3-trichloromethyl-1,2,4-thiadiazolyl (5)]-N-N'-dimethylurea can be formed from it by utilizing the process of the present invention. Also, it is preferred from an economical standpoint to employ either N-chlorotrichloromethylacetamidine or N-bromotrichloromethylacetamidine, most preferably, the former compound, as the other reactant.

The N-halotrichloroacetamidine as employed in the present reaction can be either directly added to the reaction mixture or generated in situ in this reaction mixture. The in situ generation, for example, includes either of two ways. One method is by the halogenation of trichloroacetamidine in the presence of an alkali metal hydroxide or alkaline earth hydroxide. This is illustrated by equation (2) shown below. A second method for generating N-halotrichloroacetamidine in situ is first to ammoniate trichloroacetonitrile to form trichloroacetamidine (as illustrated by equation (1) shown below). The reaction mixture containing the trichloroacetamidine is then halogenated as in the first in situ method. Both of these in situ generation methods may advantageously employ the same solvent which may be in the main reaction of the present invention (as illustrated by equation (3) shown below). Therefore, all three reactions involved herein may be carried out sequentially in the same reactor without the necessity of solvent exchange steps or intermediate isolation steps as required by the above-cited prior art method. Moreover, the overall product yields obtained by the use of these reactions are comparably higher than the prior art method discussed above. Furthermore, the employment of this combination of three reactions advantageously represents a process for producing a desired product of the present invention from trichloroacetonitrile, which is a chemical that is now availible in commercial quantities.

For illustration, the present invention may be described by the three equations set forth below. Equations (1) and (2) set forth the two modes discussed above for producing the N-halotrichloromethylacetamidine in situ. Equation (3) represents the basic reaction of the present invention.

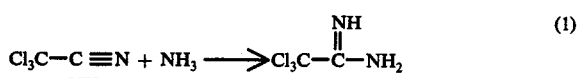
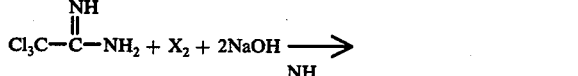
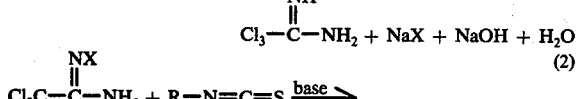
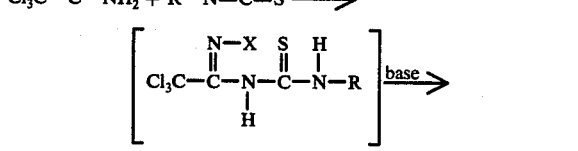

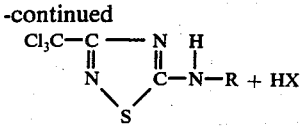

wherein R is a lower alkyl having from 1-4 carbon atoms and X is a chloro, bromo, or iodo group.

The main reaction of the present invention as illustrated by equation (3) requires the presence of a base in order to neutralize the acid HX which is also produced. Neutralization of this acid is necessary to prevent the acid from interfering with the ring-closing step. Any suitable base or aqueous solutions of base which are normally utilized for this type of reaction may be employed herein. The preferred bases are aqueous solutions of the alkali metal hydroxides such as NaOH or KOH, or aqueous solutions of alkaline earth hydroxides such as $Ca(OH)_2$ or $Mg(OH)_2$ because they may also be utilized in the in situ generation of N-halotrichloroacetamidine as shown in equation (2). The most preferred base is any aqueous solution of NaOH because of its low cost and easy use in the reaction mixture. Alternatively, if the N-halotrichloroacetamidine compound is not being generated in situ, but instead is made separately and then merely added to the reaction mixture, other types of conventional bases such as $Na_2CO_3$, $K_2CO_3$, $NaHCO_3$, and $KHCO_3$ may be utilized. The amount of base needed for this reaction should preferably be sufficient to neutralize substantially all of the acid being produced. Thus, at least a stoichiometric equivalent of base is usually added to the reaction mixture. Also, the minimum amount of base needed for this neutralization may preferably be determined by keeping the pH of the reaction mixture above about 7.0. Normally, a pH range from about 7.0 to about 10.0 would be suitable.

If the N-halotrichloroacetamidine reactant is generated in situ from trichloroacetamidine by the halogenation reaction represented by equation (2), an alkali metal hydroxide or alkaline earth hydroxide must be employed in order to create an active halogen species such as NaOX where X is a halogen. This intermediate species must first be formed by the reaction of NaOH and $X_2$ so that it in turn can react with the hydrogen on the trichloroacetamidine and thereby cause substitution of this hydrogen with a halide ion. The amount of hydroxide needed to be present during this reaction should preferably be enough to ensure substantially complete halogenation of the trichloroacetamidine according to equation (2). More preferably, the amount of hydroxide utilized in the reaction mixture should be enough (1) to ensure this substantially complete halogenation plus (2) ensure neutralization of substantially all of the acid being formed in the reaction illustrated by equation (3).

Any or all of the three reactions represented by the above equations can be preferably carried out in the presence of a suitable organic solvent such as a non-polar, water-immiscible solvent. Illustrative examples are chloroform, carbon tetrachlorine or methylene chloride. The latter solvent is most preferred because of its relative ease in handling and its lesser possibility of causing toxicity problems than the others. Polar solvents such as alcohols or ethers are not desirable because they may be easily halogenated. In a preferred embodiment of the present invention, one suitable organic solvent such as methylene chloride, is employed as the same solvent for all three reactions which are carried out sequentially in the reaction vessel.

The molar ratios between any of the reactants illustrated by equations (1), (2), or (3) are not critical to the present invention and any particular molar excess of any one reactant can be employed. However, it is preferred in most cases to use approximately the stoichiometric amounts given above in equations (1), (2), and (3). Any large molar excess of a reactant may result in an undesirable loss of the reactant in the reaction mixture, lower product yields and/or more complicated purification procedures. Therefore, it is preferred to employ no more than about 10% molar excess, more preferably, no more than about 5% molar excess, if any reactant. However, one exception to these preferred molar ratios occurs when liquid ammonia is employed in the reaction represented by equation (1).

In particular, when liquid ammonia is employed in reaction (1), it is preferred to use it in at least about a 5-fold, more preferably, from about a 5-fold to about a 20-fold, molar excess over the trichloroacetonitrile because it is more convenient to maintain the resulting product, trichloroacetamidine, in a solution of liquid ammonia rather than allow it to form a solid mass in the reaction vessel during the reaction. This excess liquid ammonia is easily removed after the reaction is over by merely increasing the temperature of the reaction mixture, for example, up to about 0° C. The liquid ammonia is thus converted to a gas and is allowed to simply bubble out of the reaction mixture. This ammonia is replaced by simultaneously adding a suitable solvent to the reaction mixture.

Other reaction parameters such as reaction temperatures, pressures, and times are generally not critical limitations and this invention is not to be limited thereby. Any suitable reaction temperatures may be employed that are conventionally used for these types of reactions. For example, it may be desirable to carry out reaction of equation (1) at about −40° C to about 0° C when liquid ammonia is used, while reactions of equations (2) and (3) may be carried out from about 0° C to about +50° C. However, temperatures down to about −70° C and up to about 100° C may be utilized. Likewise, any suitable reaction pressure may be employed. Atmospheric pressure is most preferred because it does not require any special apparatus. Further, the reaction time for each of the above-described equations normally is substantially instantaneous; however, the combining of the reactants together in the reaction vessel is normally allowed to precede very slowly to prevent uncontrolled exothermic flashing from occuring. Normally, from about 0.5 to about 3 hours addition time for each reaction is suitable.

After the completion of reaction (3), if desired, the product may be recovered by any conventional method such as standard phase separation, solvent-stripping, filtration, and crystallization procedures. In particular, one method is to strip off the organic solvent thereby leaving water slurry. This water slurry is then filtered and the resulting filter cake containing the product is then recovered after water washing to remove any water-soluble salts. Another conventional method is to add more organic solvent to dissolve the product fully in the solvent, separate any water phase, then strip off the organic solvent, thereby leaving a solid mass containing the product. The recovered product can be used as such as a fungicide.

Rather than be employed as a useful product itself, the desired 3-trichloromethyl-5-loweralkylamino-1,2,4-thiadiazole product can be converted into a desired class of pesticides and crop protection chemicals known as N-[3-trichloromethyl-1,2,4-thiadiazolyl (5)]-N-N'-di-loweralkylurea compounds. This may be accomplished by reacting them with suitable N-loweralkylisocyanates as illustrated below in equation (4):

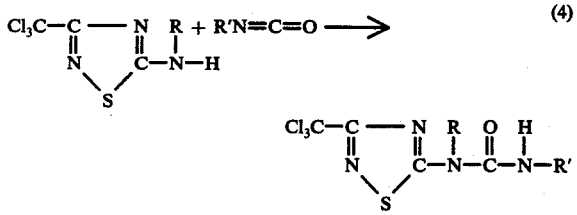

where R and R' are independently lower alkyl groups having 1-4 carbon atoms. Preferably, R and R' are the same lower alkyl group, most preferably both are methyl. However, it is not necessary that both be the same.

Besides these two classes of reactants illustrated in equation (4), the other reaction parameters such as reaction temperature, pressure, time, solvent and the like are not critical to this preferred embodiment of the present invention. In fact, any conventional reaction temperatures, pressures, times, and solvents may be utilized. In general, reaction temperatures from about 0° to about 100° C can normally be utilized. When R and R' are both methyl, it may be preferred to employ reaction temperatures from about 25° to about 50° C. Also, the reaction is most preferably carried out at atmospheric pressure because then the need for special pressure equipment can be avoided. Furthermore, any suitable times such as from 0.5 to 3 hours for adding the reactants together may be employed. Also, the reaction may be advantageously carried out in the same solvent as employed in the reaction illustrated by equation (3). In particular, one preferred embodiment is to add the N-loweralkylisocyanate to the reaction mixture employed to form the 3-trichloromethyl-5-loweralkylamino-1,2,4-thiadiazole compound in the reaction illustrated by equation (3). The N-loweralkylisocyanate is simply added after this preceding reaction is substantially completed.

After substantial completion of the reaction illustrated by equation (4), the N-[3-trichloromethyl-1,2,4,-thiadiazolyl (5)]-N-N'-di-loweralkylurea compounds can be recovered from the reaction mixture by any conventional procedures.

The present invention is further illustrated by the following examples. All percentages and proportions are by weight unless otherwise explicitly indicated.

EXAMPLE I

A 500 ml flask was charged with 24.0 g (0.10 mol) N-bromotrichloroacetamidine and 100 gm of methylene chloride. Potassium bicarbonate, 0.15 mol was dissolved in 100 ml of water then added to the reactor. Methylisothiocyanate, 7.6 g (0.105 mol), in 30 g MeCl₂ was added while stirring. An exotherm occurred (25-35° C). The mixture was stirred until all of the bromine coloration disappeared. The majority of the product was isolated by filtration, another portion by stripping the methylene chloride solution. A 75% yield of the desired product was obtained. Identification of the product was confirmed by infrared spectroscopy and mass spectroscopy. Elemental analysis was in agreement with the proposed composition.

EXAMPLE II

A 500 ml three necked flask was charged with 40.4 gm (0.25 mol) trichloroacetamidine in 150 ml of methylene chloride. Water 150 ml, and 44 g (1.08 mol) 98% NaOH was charged while keeping the reactor below 35° C. Bromine, 40 g (0.25 mol) was then added. AFter the bromination was complete, methylisothiocyanate, 18.3 g (0.25 mol) in 60 g methylene chloride was added during 0.5 hours. After stirring for two hours the reaction temperature had risen from 5° to 34° C. Gas chromatographic analysis showed that all of the N-bromotrichloroacetamidine had reacted. The organic portion was phased from the water. The water was extracted with additional methylene chloride and combined with the original organic. Yield of the 3-trichloromethyl-5-methylamino-1,2,4-thiadiazole was determined by titration with methylisocyanate. Yield of the desired compound was 73% by weight minimum.

EXAMPLE III

A 500 ml flask was fitted with a dry ice condenser, stirrer, thermometer, and gas inlet tube. Ammonia, 102 g (6.0 mol) was condensed into the flask at −70° C. After allowing the flask to warm to −50° C 144.5 g (1.0 mol) of trichloroacetonitrile was added dropwise over two hours while maintaining the reaction temperature at about −40° C. The reactor was then allowed to rise to about 15° C under a nitrogen purge. During this time the dry ice condenser was disconnected allowing the majority of the ammonia to escape. 500 g of methylene chloride was then added to the slurry and the last traces of ammonia were removed by distillation at 0° C (20 torr).

Next, 42 g (1.05 mol) of NaOH in 378 g of water was charged into this methylene chloride solution and a two-phase system was created. This two-phase system was cooled to about 5° C and 72 g (1.0 mol) chlorine was bubbled in over two hours. This reaction mixture was warmed to 25° C during 0.5-1.0 hour.

To this two-phase system was added 1.5 mol of NaOH at 20°-25° C. Cooling was employed to avoid overheating while the NaOH was being dissolved. Methylisothiocyanate, 73 g (1.0 mol) was added during two hours at about 35° C. After the addition was completed, the mixture was stirred for one hour at 35° C.

The water (upper) layer was phased from the reaction mixture and discarded. The organic methylene chloride layer was then dried by azeotropic distillation, continuously removing any water contained therein and recycling the methylene chloride. The dried methylene chloride layer (720 g) was divided into two portions of 360 g each.

One portion (360 g) of this methylene chloride layer was stripped of the methylene chloride solvent under vacuum. The solid residue (m.p. 123°-125° C) weighed 94.7 g (0.407 mol) and was identified as 3-trichloromethyl-5-methylamino-1,2,4-thiadiazole by infrared spectroscopy. Based on 0.5 mol of each reactant being employed, the yield of this product was 81.5% by weight.

EXAMPLE IV

The second portion of the methylene chloride solution obtained in Example III was added to 28.5 g (0.5 mol) of methylisocyanate at 35° for two hours. The resulting slurry was stripped of methylene chloride under vacuum (20 torr) at over a temperature range of 25° to 50° C. The resulting residue weighed 108.3 g (0.415 mol) and was identified as N-[3-trichloromethyl-1,2,4-thiadiazolyl (5)]-N,N'-dimethylurea by infrared spectroscopy. Based on 0.5 mol of each reactant being employed, the yield of this product was 83.0% by weight. The melting point of this product was 148° C and was found to be in agreement with the literature value (see U.S. Pat. No. 3,822,280, Example III).

What is claimed is:

1. A process for producing 3-trichloromethyl-5-loweralkylamino-1,2,4-thiadiazole compounds comprising
reacting an N-loweralkylisothiocyanate with an N-halotrichloroacetamidine in the presence of a base to form said 3-trichloromethyl-5-loweralkylamino-1,2,4-thiadiazole compound.

2. The process of claim 1 wherein said N-loweralkylisothiocyanate is N-methylisothiocyanate.

3. The process of claim 1 wherein said N-halotrichloroacetamidine is selected from the group consisting of N-chlorotrichloroacetamidine and N-bromotrichloroacetamidine.

4. The process of claim 1 wherein said base is NaOH.

5. The process of claim 1 wherein the temperature of said reaction is from about 0° to about 50° C.

6. The process of claim 1 wherein said reaction is carried out in the presence of non-polar, water-immiscible organic solvent.

7. The process of claim 6 wherein said N-halotrichloroacetamidine is generated in situ by the halogenation of trichloroacetamidine in the presence of a base selected from the group consisting of alkali metal hydroxides and alkaline earth hydroxides.

8. The process of claim 7 wherein said trichloroacetamidine is generated in situ by the reaction of trichloroacetonitrile with ammonia.

9. The process of claim 7 wherein said halogen employed in said halogenation reaction is selected from the group consisting of chlorine and bromine.

10. The process of claim 9 wherein said halogenation reaction occurs in the presence of sodium hydroxide.

11. The process of claim 10 wherein said trichloroacetamidine is generated in situ by the reaction of trichloroacetonitrile with ammonia.

12. The process of claim 11 wherein said organic solvent is methylene chloride.

13. The process of claim 12 wherein said ammonia is liquid ammonia.

14. A process of producing an N-[3-trichloromethyl-1,2,4-thiadiazolyl (5) ]-N,N'-di-loweralkylurea compound by reacting a loweralkylisocyanate with said 3-trichloromethyl-5-loweralkylamino-1,2,4-thiadiazole produced by the process of claim 1.

15. The process of claim 14 wherein said N-halotrichloroacetamidine is generated in situ by the halogenation of trichloroacetamidine in the presence of a base selected from the group consisting of alkali metal hydroxides and alkaline earth hydroxides.

16. The process of claim 15 wherein said trichloroacetamidine is generated in situ by the reaction of trichloroacetonitrile with ammonia.

17. The process of claim 16 wherein said reactions are carried out in a non-polar, water-immiscible organic solvent.

18. The process of claim 17 wherein said 5-trichloromethyl-3-loweralkylamino-1,2,4-thiadiazole is 5-trichloromethyl-3-methyl-1,2,4-thiadiazole.

19. The process of claim 18 wherein said N-loweralkylisocyanate is N-methylisocyanate.

20. The process of claim 19 wherein said organic solvent is methylene chloride.

21. The process of claim 20 wherein said base is sodium hydroxide.

22. The process of claim 21 wherein said halogen employed in said halogenation reaction is selected from the group consisting of chlorine and bromine.

* * * * *